United States Patent [19]
Renfroe

[11] Patent Number: 4,460,777
[45] Date of Patent: Jul. 17, 1984

[54] N-SUBSTITUTED-2-PYRIDYLINDOLES

[75] Inventor: Harris B. Renfroe, West Nyack, N.Y.

[73] Assignee: Ciba-Geigy Corporation, Ardsley, N.Y.

[21] Appl. No.: 419,383

[22] Filed: Sep. 17, 1982

Related U.S. Application Data

[62] Division of Ser. No. 323,018, Nov. 19, 1981, abandoned.

[51] Int. Cl.$^3$ .......................................... C07D 401/04
[52] U.S. Cl. .................................................. 546/273
[58] Field of Search ........................ 546/273; 424/263

[56] References Cited

U.S. PATENT DOCUMENTS

| | | | |
|---|---|---|---|
| 3,182,071 | 5/1965 | Shauel et al. | 546/273 |
| 3,285,908 | 11/1966 | Shen et al. | 546/273 |
| 3,468,894 | 9/1969 | Pfenninger | 546/273 |
| 3,491,114 | 1/1970 | Suh | 260/326 |
| 3,557,142 | 1/1971 | Bell et al. | 546/273 |
| 4,217,357 | 8/1980 | Cross et al. | 424/273 R |
| 4,226,878 | 10/1980 | Itzuka et al. | 424/273 R |
| 4,256,757 | 3/1981 | Hayashi et al. | 424/273 R |
| 4,273,782 | 6/1981 | Cross et al. | |
| 4,343,811 | 9/1982 | Hurnaus et al. | 424/274 |
| 4,363,912 | 12/1982 | Cross et al. | |

FOREIGN PATENT DOCUMENTS

| | | |
|---|---|---|
| 0003901 | 9/1979 | European Pat. Off. . |
| 54417 | 6/1982 | European Pat. Off. . |
| 6717904 | 9/1967 | Japan . |
| 2016452 | 9/1979 | United Kingdom . |

OTHER PUBLICATIONS

Buchmann, 2-Pyridylindoles Pharmazie 23, 557–60, (1968), C.A. 70 472,365, (1969).
Sugasawa et al., Pharm. Bull. Japan 4, 16–19, (1956).
Buchmann et al., C.A. 64,19540d, (1966).
Kahnt et al., Acta Endocrinologia 70, (1972), pp. 315–330.
Fetizon et al., Bull. Soc. Chim., France 1969, 4154–4159.
Takahashi et al., Chem. Abstracts, 1964, 1694d.
Fetizon et al., Bull. Soc. Chim., France, 1966, 771–2.
Bull. Soc. Chim., France, 1969, 4155, Fetizon et al.

Primary Examiner—John M. Ford
Assistant Examiner—J. G. Mullins
Attorney, Agent, or Firm—Norbert Gruenfeld

[57] ABSTRACT

Various 1-carboxylic acid substituted-2-pyridylindoles and functional derivatives thereof are highly specific thromboxane synthetase inhibitors. Synthesis of, pharmaceutical compositions thereof, and methods of treatment utilizing such compounds are included.

2 Claims, No Drawings

N-SUBSTITUTED-2-PYRIDYLINDOLES

This is a divisional of application Ser. No. 323,018 filed Nov. 19, 1981 now abandoned.

BACKGROUND OF THE INVENTION

U.S. Pat. No. 3,468,894 disclosed the 1-unsubstituted 3-methyl-2-(3- or 4-pyridyl)indoles as diuretic agents. 2-(2-Pyridyl)indole-3-(acetic, propionic) acids are reported e.g., in Pharm. Bull. 4, 16 (1956) and Chemical Abstracts 64, 19540d (1966) respectively. Various optionally substituted 2-(3-pyridyl) indole-3-acetic acids have been described as chemical intermediates in Bull. Soc. Chim. France 1966, 771-2 and Bull. Soc. Chim. France 1969, 4154-9. The preparation of 1-cyanoethyl-2-(2-pyridyl) indole is reported in Pharmazie 23 (10), 557-60 (1968).

Reported as thromboxane synthetase inhibitors are e.g., 3-(imidazol-1-yl-alkyl)indoles of U.S. Pat. No. 4,217,357 and 1-substituted imidazoles of U.S. Pat. No. 4,256,757 and British Patent Application No. 2,016,452A.

The present invention is concerned with N-(or 1)-substituted-2-pyridylindoles of formula I representing a novel class of pharmaceuticals. For example, the compounds of formula I are surprisingly potent and highly specific thromboxane synthetase inhibitors.

The foregoing attributes render the N-substituted-2-pyridyl indoles of this invention particularly useful when administered, alone or in combination, to mammals, e.g. for the treatment or prevention of diseases responsive to the inhibition of thromboxane synthetase, comprising cardiovascular disorders such as thrombosis, atherosclerosis, coronary spasm, cerebral ischaemic attacks, migraine and other vascular headaches, myocardial infarction, angina pectoris, hypertension; respiratory disorders, such as asthma; and inflammatory disorders. Inhibition of thromboxane synthetase also has been noted to decrease metastasis in certain classes of tumors, and the compounds of this invention may thus be useful for the treatment of certain carcinomas.

SUMMARY OF THE INVENTION

This invention relates to N(or 1)-substituted-2-pyridyl indoles of formulas I which are useful as selective thromboxane synthetase inhibitors, processes for preparing same, pharmaceutical compositions comprising said compounds, and methods for treating syndromes, conditions and diseases in mammals responsive to the inhibition of thromboxane synthetase by administration of said compounds and compositions.

Particularly the invention relates to the 1-substituted 2-pyridyl indoles of formula I

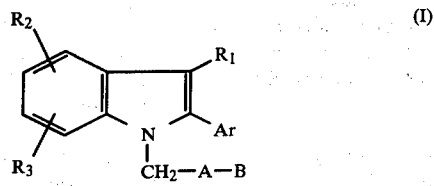

wherein
$R_1$ represents hydrogen or lower alkyl;

Ar represents pyridyl unsubstituted or substituted by lower alkyl, carboxy, lower alkoxycarbonyl or carbamoyl;

$R_2$ and $R_3$ independently represent hydrogen, lower alkyl, halogen, trifluoromethyl, hydroxy lower alkoxy, carboxy lower alkyl or lower alkoxycarbonyl lower alkyl, carboxy or lower alkoxycarbonyl;

A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene or a direct bond;

B represents carboxy, lower alkoxycarbonyl, carbamoyl, mono- or di-tower alkylcarbamoyl, or hydroxymethyl; the N-oxides thereof; and pharmaceutically acceptable salts thereof.

DETAILED DESCRIPTION OF THE INVENTION

Preferred embodiments of this invention relate to compounds of formula I wherein
$R_1$ represents hydrogen or lower alkyl;
Ar represents 2-, 3- or 4-pyridyl or 2-, 3- or 4-pyridyl substituted by lower alkyl;
$R_2$ is hydrogen, lower alkyl, halogen, trifluoromethyl, hydroxy, lower alkoxy, carboxy lower alkyl or lower alkoxycarbonyl lower alkyl;
$R_3$ is hydrogen;
A represents straight chain or branched alkylene of 1 to 12 carbon atoms, phenylene, lower alkylenephenylene of 7 to 10 carbon atoms, or a direct bond;
B represents carboxy, lower alkoxycarbonyl, carbamoyl or hydroxymethyl; the N-oxides thereof; and pharmaceutically acceptable salts thereof.

Further preferred are said compounds wherein $R_2$ is attached at the 5-position of the indole nucleus.

Very useful as thromboxane synthetase inhibitors are compounds of formula I wherein A represents straight chain or branched alkylene of 1 to 12 carbon atoms or phenylene.

Particularly useful are compounds of formula II

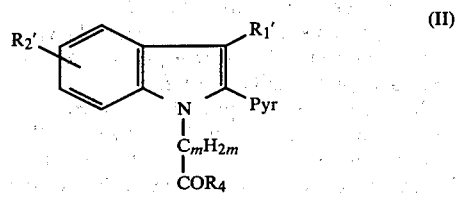

wherein
$R_1'$ represents hydrogen or lower alkyl;
$R_2'$ represents hydrogen, lower alkyl, halogen, trifluoromethyl, hydroxy or lower alkoxy;
Pyr represents 2-, 3- or 4-pyridyl; m represents an integer from 1 to 13;
$R_4$ represents hydroxy, lower alkoxy or amino; and pharmaceutically acceptable salts thereof.

Especially valuable are compounds of formula II wherein
$R_1'$ represents methyl, ethyl, propyl;
$R_2'$ represents hydrogen, methyl, chloro, fluoro, trifluoromethyl, hydroxy or methoxy;
m represents an integer from 3 to 10;
$R_4$ represents hydroxy, ethoxy, methoxy or amino;
Pyr represents 3- or 4-pyridyl; and pharmaceutically acceptable salts thereof.

Most preferred are the compounds of formula II wherein $R_1'$ represents methyl, $R_2'$ represents hydrogen, m is 4 to 8, Pyr represents 3- or 4-pyridyl, and $R_4$ represents hydroxy, ethoxy, methoxy or amino.

Particularly useful are also compounds of formula III

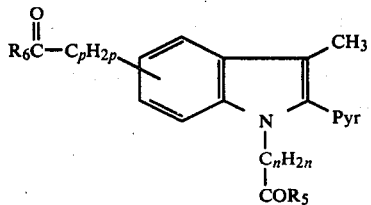

wherein
n represents an integer from 3 to 10;
p represents an integer from 0 to 4;
Pyr represents 2-, 3- or 4-pyridyl;
$R_5$ and $R_6$ independently represent hydroxy or lower alkoxy; and pharmaceutically acceptable salts thereof.

Preferred are compounds of formula III wherein n is 4 to 8, p is 1 to 4; Pyr is 3- or 4-pyridyl; $R_5$ and $R_6$ represent hydroxy.

Also valuable are compounds of formula IV

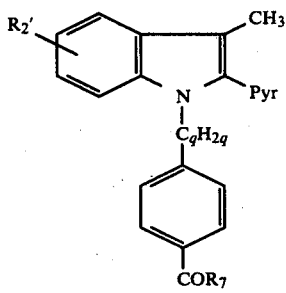

wherein
$R_2'$ represents hydrogen, methyl, chloro, fluoro, trifluoromethyl, hydroxy or methoxy;
q represents an integer from 1 to 4;
$R_7$ represents hydroxy or lower alkoxy;
Pyr represents 2-, 3- or 4-pyridyl; and pharmaceutically acceptable salts thereof.

Preferred are compounds of formula IV wherein $R_2'=H$; q=1 Pyr=3- or 4-pyridyl; and $R_7$=hydroxy.

The general definitions used herein have the following meanings within the scope of the present invention.

A straight chain or branched alkylene represents $C_{1-12}$ alkylene preferably propylene, butylene, pentylene, hexylene, or heptylene, said radicals being unsubstituted or substituted by one or more lower alkyl groups with the proviso that the total number of carbon atoms equals no more than 12.

The term "straight chain or branched alkenylene" represents $C_{2-12}$ alkenylene groups preferably propenylene, 1- or 2-butenylene, 1- or 2-pentenylene, 1-, 2- or 3-hexenylene, 1-, 2-, 3 or 4-heptenylene, said groups being unsubstituted or substituted by one or more lower alkyl groups with the proviso that the total number of carbon atoms equals no more than 12.

The term "straight chain or branched alkynylene" represents $C_2$–$C_{12}$ alkynylene preferably propynylene, 1- or 2-butynylene, 1- or 2-pentynylene, 1-, 2- or 3-hexynylene, 1-, 2-, 3- or 4-heptynylene, said radicals being unsubstituted or substituted by one or more lower alkyl groups with the proviso that the total number of carbon atoms equals no more than 12. The term phenylene represents 1,2-, 1,3- and preferably 1,4-phenylene. The term pyridyl represents 2-, 3- and 4-pyridyl, preferably 3-pyridyl.

The term "lower" when referred to above and hereinafter in connection with organic groups, radicals or compounds respectively defines such with up to and including 7, preferably up to and including 4 and advantageously one, two or three carbon atoms.

A lower alkylenephenylene group, a phenylene lower alkylene group or a lower alkylenephenylene lower alkylene group preferably contains 1 to 4 carbon atoms and advantageously one or two carbon atoms in each alkylene portion.

A lower alkyl group preferably contains 1–4 carbon atoms and represents for example ethyl, propyl, butyl or advantageously methyl.

A lower alkoxy group preferably contains 1–4 carbon atoms and represents for example, ethoxy, propoxy or advantageously methoxy.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl. A mono(lower alkyl) carbamoyl group preferably contains 1–4 carbon atoms in the alkyl portion and is for example N-methylcarbamoyl, N-propylcarbamoyl, or advantageously N-ethylcarbamoyl. A di(lower alkyl) carbamoyl group preferably contains 1–4 carbon atoms in each lower alkyl portion and represents for example N,N-dimethylcarbamoyl, N-methyl-N-ethylcarbamoyl and advantageously N-N-diethylcarbamoyl.

Halogen is preferably fluorine and chlorine, but may also represent bromine or iodine.

Pharmaceutically acceptable salts are preferably metal or ammonium salts or said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium hydroxides, e.g., methylamine, diethylamine, triethylamine, dicyclohexylamine, triethanolamine, ethylenediamine, tris-(hydroxymethyl)aminomethane or benzyltrimethylammonium hydroxide. Said compounds of Formula I form acid addition salts of preferably the pharmaceutically acceptable inorganic or organic acids, such as of strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of this invention exhibit valuable pharmacological properties, e.g. cardiovascular effects, by selectively decreasing thromboxane levels through selective inhibition of thromboxane synthetase in mammals. The compounds are thus useful for treating diseases responsive to thromboxane synthetase inhibition in mammals, primarily cardiovascular disorders such as thrombosis, atherosclerosis, coronary spasm, cerebral ischaemic attacks, migraine and other vascular headaches, myocardial infarction, angina pectoris, and hypertension.

These effects are demonstrable in in vitro tests or in vivo animal tests using advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 to 100 mg/kg/day, preferably between about 0.05 and 50 mg/kg/day, advantageously between about 0.1 and 25 mg/kg/day.

The in vitro inhibition of the thromboxane synthetase enzyme can be demonstrated, analogous to the method of Sun, Biochem. Biophys. Res. Comm. 74, 1432 (1977); the testi g procedure is as follows:

$^{14}$C-Archidonic acid is incubated with an enzyme consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin E2 ($PGE_2$) is reduced to a mixture of Prostaglandin $F_2\alpha$ and $F_2\beta$ ($PGF_2\alpha+\beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene:acetone:glacial acetic acid (100 volumes:100 volumes:3 volumes). The radioactive zones are located; those corresponding to Thromboxane $B_2$ ($TxB_2$) and $PGF_2\alpha+\beta$ are transferred to liquid scintillatiopn vials and counted. The ratio of counts for $TxB_2/PGF_2\alpha+\beta$ is calculated for each concentration of test compound and $IC_{50}$ values are determined graphically as the concentration of test compound at which the ratio of $TxB_2/PGF_2\alpha+\beta$ is reduced to 50% of the control value.

The in-vitro effect on prostaglandin cyclooxygenase is measured by a modification of the method of Takeguchi et al. described in Biochemistry 10, 2372 (1971); the testing procedure is as follows:

Lyophilized sheep seminal vesicle microsomes are utilized as the prostaglandin-synthesizing enzyme preparation. The conversion of $^{14}$C-arachidonic acid to $PGE_2$ is measured. Test compounds (dissolved in buffer, or if necessary, in small amount of ethanol) are added to the incubation mixture. The prostaglandins are extracted and separated by thin-layer chromatography; the plates are scanned, the radioactive zones corresponding to $PGE_2$ are transferred to liquid scintillation vials and counted for radioactivity. $IC_{50}$ values for inhibition are determined graphically as the concentration of test compound causing a 50% reduction in the amount of $PGE_2$ synthesized.

The in-vitro effect on prostacyclin ($PGI_2$) synthetase is measured analogous to the method of Sun et al., Prostaglandins 14, 1055 (1977);

The testing procedure is as follows:

$^{14}$C-Arachidonic acid is incubated with an enzyme mixture consisting of solubilized and partially purified prostaglandin cyclo-oxygenase from sheep seminal vesicles and crude $PGI_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described in Sun et al. The radioactive zones are located with a scanner; those corresponding to 6-keto-$PGF_1\alpha$ (a stable end product of prostacyclin biotransformation) and $PGE_2$ are transferred to liquid scintillation vials and counted. The ratio of counts for 6-keto-$PGF_1\alpha/PGE_2$ is calculated for each concentration of test compound used. $IC_{50}$ values for inhibition are determined graphically as the concentration of test compound at which the ratio of 6-keto-$PGF_1\alpha/PGE_2$ is reduced to 50% of the control value.

The inhibition of the synthesis and the reduction of plasma levels of thromboxane is determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane $B_2$ and another aliquot for 6-keto-$PGF_1\alpha$, the stable metabolites of thromboxane $A_2$ and prostacyclin ($PGI_2$) respectively, by radioimmunoassay.

Compounds of the formula I are very potent and selective, thromboxane synthetase inhibitors. At and above the effective dose levels for thromboxane synthetase inhibition neither the beneficial prostacyclin synthetase enzyme system nor the prostaglandin cyclooxygenase enzyme system is significantly inhibited. Surprisingly, the prostacyclin levels are significantly increased.

Illustrative of the invention, the $IC_{50}$ for 1-(7-carboxyheptyl)-3-methyl-2-(3-pyridyl)indole of example 1 is $1.2\times10^{-8}M$ for thromboxane synthetase inhibition whereas the $IC_{50}$ for both inhibition of prostacyclin synthetase and cyclooxygenase is several orders of magnitude higher, i.e. about $1\times10^{-4}M$.

Furthermore the $IC_{50}$ for thromboxane synthetase inhibition is $2\times10^{-8}M$ for compound of example 9, namely 1-(5-carboxypentyl)-5-(2-carboxyethyl)-3-methyl-2-(3-pyridyl)indole, and $5\times10^{-8}M$ for 1-(4-carboxybenzyl)-3-methyl-2-(3-pyridyl)indole, the compound of example 11, $1\times10^{-9}M$ for 1-(5-carboxypentyl)-5-chloro-3-methyl-2-(3-pyridyl)indole, the compound of example 7, and $1\times10^{-8}M$ for 1-(5-carbamoylpentyl)-5-chloro-3-methyl-2-(3-pyridyl)indole, the compound of example 13.

1-(7-Carboxyheptyl-3-methyl-2-(3-pyridyl)indole of example 1, a representative compound of the invention, decreases the plasma concentration of thromboxane $B_2$ by over 50% in the rat at an oral dose as low as 0.10 mg/kg; a surprising increase in the plasma level of prostacyclin is observed at this or a higher dose thereof.

The aforementioned advantageous properties render the compounds of this invention of great value as specific therapeutic agents for mammals including man.

Indicative of the utility in thromboembolism, compounds of this invention, e.g. 1-(7-carboxyheptyl)-3- methyl-2-(3-pyridyl) indole of example 1 inhibits variously induced platelet aggregation and thrombocytopenia. Experimentally, prolongation of bleeding time in the rat is indicative of a beneficial antithrombotic effect. The compounds of this invention prolong bleeding time, e.g. 1-(7-carboxyheptyl)-3-methyl-2-(3-pyridyl) indole of example 1 prolongs bleeding time when administered orally to rats at a dose of about 30 mg/kg.

Indicative of the beneficial effect in respiratory disorders, the compounds of this invention afford protection against sudden death due to arachidonic acid induced pulmonary obstruction, e.g. 1-(7-carboxyheptyl)-3-methyl-2-(3-pyridyl) indole of example 1 protects against sudden death when administered orally to mice at a dose of 100 mg/kg.

In addition to the pharmaceutically acceptable salts cited above, any prodrug derivatives thereof, e.g., pharmaceutically acceptable esters and amides of the carboxylic acids of this invention that may be convertible by solvolysis or under physiological conditions to the said carboxylic acids, represent a further object of this invention.

Said esters are preferably e.g., the straight chain or branched lower alkyl esters unsubstituted or suitably substituted such as the pivaloyloxymethyl, 2-diethylaminoethyl, α-carboxyethyl or suitably esterified α-carboxyethyl esters and the like which are prepared by methods well known to the art.

Said amides are preferably e.g. simple primary and secondary amides and amides derived from the amino acids or derivatives thereof, such as the amides derived from alanine, phenylalanine and the like.

The compounds of formula I are advantageously prepared according to the following process:

(a) Condensing preferably under basic conditions a compound of the formula V

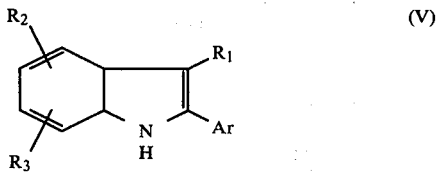

(V)

wherein

R$_1$ represents hydrogen or lower alkyl;

Ar represents pyridyl or pyridyl substituted by lower alkyl, carboxy, lower alkoxycarbonyl or carbamoyl;

R$_2$ and R$_3$ represent hydrogen, lower alkyl, halogen, trifluoromethyl, hydroxy, lower alkoxy, carboxy lower alkyl or lower alkoxycarbonyl lower alkyl, carboxy or lower alkoxycarbonyl; with a reactive functional derivative of a compound of the formula VI

HOCH$_2$—A—B'     (VI)

wherein

A represents straight chain or branched alkylene of 1 to 12 carbon atoms, alkenylene of 2 to 12 carbon atoms, alkynylene of 2 to 12 carbon atoms, lower alkylenephenylene lower alkylene, lower alkylenephenylene, phenylene lower alkylene, phenylene or a direct bond; and B' represents carboxy, lower alkoxycarbonyl, carbamoyl, mono- or di-lower alkylcarbamoyl, hydroxymethyl, etherified hydroxymethyl, halomethyl, trialkoxymethyl or cyano; to yield a compound of formula Ia

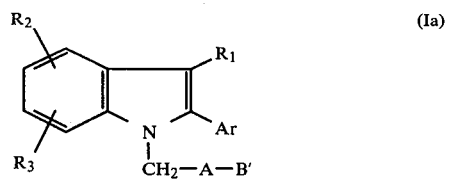

wherein

Ar, R$_1$, R$_2$, R$_3$, A and B' have meanings as defined above;

(b) optionally hydrolyzing or derivatizing the resulting product; and (c) converting any resulting compound into another compound of formula I.

Indoles of formula V are converted preferably in situ, to reactive organometallic intermediates with a reactive metallizing agent, preferably about one molar equivalent of e.g. a strong alkali metal base, such as lithium diisopropylamide, sodium hydride, potassium t-butoxide in an inert solvent such as dimethylformamide or tetrahydrofuran at a temperature range between −50° to +75° preferably between −25° and +50°. Condensation of the resulting reactive organometallic reagent with a reactive functional derivative of a compound of formula VI proceeds at a temperature range from about −25° to +50° preferably at a temperature range of 0° to 30°. In the case where B' represents carboxy, carbamoyl, mono lower alkyl-carbamoyl, additional, e.g. one molar equivalent, metallizing agent is required.

Intermediates of formula V are either known to the art (e.g. U.S. Pat. No. 3,468,894; J. Chem. Soc. 1955, 2865; Bull. Soc. Chim. France 1969, 4154) or are prepared analogously from the corresponding optionally substituted phenylhydrazines and ketones of the formula ArCOCH$_2$R$_1$ in the presence of a condensing agent, e.g. ethanolic HCl or polyphosphoric acid by the well-known Fischer indole synthesis.

The resulting novel starting materials, e.g. those of formula Va

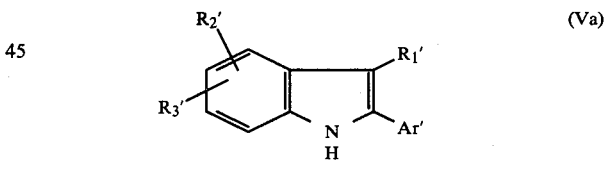

wherein

R$_1'$ represents hydrogen or lower alkyl;

Ar' represents pyridyl;

R$_2'$ represents carboxy lower alkyl, lower alkoxycarbonyl lower alkyl, carboxy or lower alkoxycarbonyl; and R$_3'$ represents hydrogen; are useful for the preparation of the correspondingly substituted compounds of formula I, e.g. compounds of formula III.

The starting materials of formula VI are known or if new, are prepared according to conventional methods, e.g. the methods illustrated in U.S. Pat. No. 4,256,757, British patent application No. 2,016,452A or as described in the examples herein.

Certain terms used in the foregoing processes have the meanings as defined below.

Reactive functional derivatives of alcohols of formula VI are e.g. such esterified by a strong inorganic or organic acid above all a hydrohalic acid, e.g. hydrochloric, hydrobromic or hydriodic acid, an aliphatic or aromatic sulfonic acid, e.g. methanesulfonic acid, p-toluenesulfonic acid, and are prepared by methods known in the art.

Trialkoxymethyl represents preferably tri(lower alkoxy)-methyl, particularly triethoxy- or trimethoxymethyl.

Etherified hydroxymethyl represents preferably tertiary lower alkyloxymethyl, lower alkoxyalkoxymethyl such as methoxymethyloxymethyl, 2-oxa- or 2-thiacycloalkoxymethyl particularly 2-tetrahydropyranyloxymethyl.

Halomethyl represents especially chloromethyl but may also be bromomethyl or iodomethyl.

An alkali metal represents preferably lithium but may also be potassium or sodium.

The optional steps of hydrolyzing or derivatizing the initial product [part a] of the aforesaid process and the conversion of the resulting product into another compound of this invention are performed by chemical methodology known to the art.

Hydrolysis of intermediates of formula Ia wherein B' represents trialkoxymethyl to compounds of formula I wherein B is carboxy is advantageously carried out with inorganic acids such as hydrohalic or sulfuric acid. Hydrolysis of intermediates wherein B' represents etherified hydroxymethyl to compounds of formula I wherein B represents hydroxymethyl is preferably carried out with solutions of inorganic acids such as a hydrohalic acid.

The compounds of formula Ia wherein B' is halomethyl are converted to compounds of formula I, wherein B is carboxy and the chain length is extended by two carbons, by first treating with e.g. a di(lower)alkylmalonate followed by hydrolysis and decarboxylation under standard conditions.

Intermediates of formula Ia wherein B' is halomethyl may be reacted preferably with a alkali metal cyanide such as potassium cyanide in a conventional manner to yield the compounds of formula Ia wherein the chain is extended by 1 carbon atom and B' is cyano. These in turn are converted to compound of formula I wherein B is carboxy, alkoxycarbonyl or carbamoyl using methods known to the art.

Compounds of formula I wherein B is lower alkoxycarbonyl may be amidized with ammonia, mono- or di-(lower)alkylamines to yield compounds of formula I wherein B represents unsubstituted, mono- or di-(lower)alkylcarbamoyl.

The compounds of formula Ia wherein B' represents unsubstituted carbamoyl may be dehydrated to the corresponding nitriles by methods known to the art. Conversion of compounds of formula Ia wherein B is lower alkoxycarbonyl; cyano; unsubstituted, mono- or di-(lower alkyl)carbamoyl to compounds of formula I wherein B represents carboxy is advantageously carried out by hydrolysis with inorganic acids such as hydrohalic or sulfuric acid or with aqueous alkalies preferably alkali metal hydroxides such as lithium or sodium hydroxide.

Compounds of formula I wherein B represents carboxy or lower alkoxycarbonyl may be reduced with simple or complex light metal hydrides such as lithium hydride, alane or diborane to compounds of formula I wherein B is hydroxymethyl. Said alcohols are also obtained by appropriate solvolysis of compounds of formula Ia wherein B' is halomethyl.

Said alcohols may in turn be transformed to the compounds of formula I wherein B is carboxy with conventional oxidizing agents.

Free carboxylic acids may be esterified with unsubstituted or substituted lower alkanols or diazo(lower)alkanes to give the corresponding esters, namely compounds of formula I wherein B is lower alkoxycarbonyl. Furthermore, the free carboxylic acids may be converted via reactive intermediates to compounds of formula I wherein B represents unsubstituted, mono or di-(lower)alkylcarbamoyl.

Compounds of formula I wherein B represents mono(lower)alkylcarbamoyl may be converted to compounds of formula I wherein B is di(lower)alkylcarbamoyl by treatment of the former with a strong base e.g. sodium hydride followed by an alkylating agent, e.g. a lower alkyl halide in an inert solvent, e.g. dimethylformamide.

Furthermore compounds of formula I wherein A represents a straight chain or branched alkynylene or alkenylene may be converted by catalytic hydrogenation e.g. under neutral conditions to compounds of formula I wherein A represents straight chain or branched alkylene.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably at the boiling point of the solvents used, and at atmospheric or superatmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of optical isomers such as racemates, mixtures of diastereoisomers, mixtures of racemates or mixtures of geometrical isomers. The aforesaid possible isomers or mixtures thereof are within the purview of this invention; certain particular isomers may be preferred.

Any resulting mixtures of diastereoisomers, mixtures of racemates and geometric isomers can be separated on the basis of the physicochemical differences of the constituents, in known manner, into the pure isomers, diastereoisomers, racemates, or geometric isomers, for example by chromatography and/or fractional crytallisation.

Any resulting racemates can be resolved into the optical antipodes by known methods, for example by e.g. reacting an acidic end product with an optically active base that forms salts with the racemic acid, and separating the salts obtained in this manner, for example by fractional crystallization, into the diastereoisomeric salts from which the optically active carboxylic acid antipodes can be liberated on acidification. The basic racemic products can likewise be resolved into the optical antipodes, e.g. by separation of the diastereoisomeric salts thereof with an optically active acid, and liberating the optically active basic compound by treatment with a standard base. Racemic products of the invention can thus be resolved into their optical antipodes, e.g., by the fractional crystallization of d- or l-(tartrates, mandelates, camphorsulfonates, or of d- or l-($\alpha$-methylbenzylammonium, cinchonidine, cinchonine, quinine, quinidine, ephedrine, dehydroabiethylamine, brucine or strychnine)salts. Advantageously, the more active of the two antipodes is isolated.

Finally, the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein B represents carboxy can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, and parenteral administration to mammals, including man, for the treatment or prevention of diseases responsive to inhibition of thromboxane synthetase, comprising an effective amount of a pharmacologically active compound of formula I, or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tables and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired (d) disintegrants, e.g. starches agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

Dimethylformamide (1640 ml) was charged into a 20 gallon glass kettle along with 430 g of potassium t-butoxide. This solution was stirred under nitrogen and cooled to −8°. A solution of 682 g of 3-methyl-2-(3-pyridyl)indole in 3280 ml of dimethylformamide was added over 0.75 hour while the temperature is maintained below 0°. After 2 hours of stirring of −10°, 1640 ml of a solution of 780 g of methyl 8-bromooctanoate in dimethylformamide was added over 1 hour. Reaction temperature was maintained below 0°. After 2 hours stirring, the reaction mixture was allowed to warm to room temperature overnight. The rust-colored mixture was then cooled to about 5° and treated with 19.7 L of ice water. The temperature rose to 25°. After 0.5 hour stirring, the mixture was extracted with 2×8 L of ether. The extracts were dried (MgSO$_4$) and concentrated in vacuo to give the methyl ester of 1-(7-methoxycarbonylheptyl)-3-methyl-2-(3-pyridyl)indole as an oil. 1293 g of this oil was treated with 6.53 L of 1N NaOH and warmed over steam to 90° for 2.5 hours. After cooling to room temperature, the solution was washed with 3×3 L of ether. The aqueous layer was cooled to 10° and acidified to pH 3.5 with 3.4 L of 2N HCl. The heavy suspension which resulted was extracted with 4×4 L of methylene chloride. The combined extracts were washed once with 4 L of water and dried (MgSO$_4$). After filtration and evaporation of solvent in vacuo at 60°, ether (1.5 L) trituration of the residue and drying gave 1-(7-carboxyheptyl)-3-methyl-2-(3-pyridyl)indole, m.p. 113°–115°. Recrystallization from ethanol raised melting point to 114°–116°.

The starting 3-methyl-2-(3-pyridyl)indole was prepared essentially as described in U.S. Pat. No. 3,468,894.

Methyl 8-bromooctanoate was prepared from azelaic acid essentially as described in U.S. Pat. No. 3,852,419, or by direct esterification of 8-bromooctanoic acid as follows:

Methanol (4.7 L), 8-bromooctanoic acid (0.912 kg) and sulfuric acid (0.912 L) were charged into a suitable reactor and the mixture was heated at reflux temperature for 5 hours and was then stirred at ambient temperature overnight. The solvent was removed at reduced (3 mm Hg) pressure and the oily residue was dissolved in ether (4 L). The solution was washed with water (3×2 L), saturated NaHCO$_3$ solution (1 L) and brine (1 L). The ether portion was dried (MgSO$_4$) and filtered to remove dessicant. Evaporation of solvent followed by distillation of the crude oil gave methyl 8-bromooctanoate, b.p. 73°–76°/0.05 mm Hg, $n_D^{23}$ 1.4614.

EXAMPLE 2

To a suspension of 4.8 g of a 50% sodium hydride suspension in mineral oil dissolved in 40 ml of dimethylformamide under nitrogen was added dropwise a solution of 13.5 g of 3-methyl-2-(3-pyridyl)indole in 80 ml of dimethylformamide. After addition was completed, the greenish yellow mixture was stirred at room temperature for about 1 hour. Ethyl bromoacetate (11.2 ml, 0.10 mole) was added dropwise to the reaction mixture which was cooled to 0°–5°, and the resulting reaction mixture was stirred at room temperature for 4 hours.

The reaction mixture was poured into 1 L of ice-water and was extracted with 3×300 ml of ether. The ether layer was extracted with 3×300 ml of 1N hydrochloric acid. The acidic extract was adjusted to pH 9-10 with concentrated ammonium hydroxide and extracted with 3×250 ml of ether. The combined ether extracts were dried (MgSO$_4$), filtered, and concentrated under vacuum to give 1-ethoxycarbonylmethyl-3-methyl-2-(3-pyridyl)indole as an oil.

This oil was heated at reflux for 4 hours in 500 ml of 1N hydrochloric acid. After standing at room temperature overnight a yellow solid was collected and dried at 60°–80°/30 mm for 12 hours. Recrystallization from ethanol gave 1-carboxymethyl-3-methyl-2-(3-pyridyl)indole hydrochloride, m.p. 204°–7°.

If the free amino acid is desired, it may be obtained by adjusting the pH of the hydrolysis medium to pH 3.5.

EXAMPLES 3–6

Utilizing the procedures of examples 1 and 2, the following compounds of formula II in which $R_1' = CH_3$, $R_2' = H$ and $R_4 = OH$ were prepared:

| Example | Starting Ester | $C_mH_{2m}$ | Pyr | M.P., °C. | Recrystallization Solvent |
| --- | --- | --- | --- | --- | --- |
| 3 | Br(CH$_2$)$_5$COOEt | (CH$_2$)$_5$ | 3-pyridyl | 113–4 | acetonitrile |
| 4 | Br(CH$_2$)$_6$COOMe | (CH$_2$)$_6$ | 3-pyridyl | 106-7.5 | acetonitrile |
| 5 | Br(CH$_2$)$_4$COOMe | (CH$_2$)$_4$ | 3-pyridyl | 123–5 | ethanol |
| 6 | Br(CH$_2$)$_5$COOEt | (CH$_2$)$_5$ | 4-pyridyl | 186–8 | acetonitrile |

The starting 2-(3- and 4-pyridyl)indoles were prepared according to U.S. Pat. No. 3,468,894.

The starting ethyl or methyl ω-bromo esters were obtained commercially or were prepared from the commercially available ω-bromoacids are illustrated below for methyl 6-bromohexanoate. A solution of 6-bromohexanoic acid (10 g) in 50 ml of methanol to which was added 1.0 ml of concentrated sulfuric acid was heated under reflux for 8 hours. The methanol was distilled off, the residue was dissolved in ether. The ether solution was washed free of acid with water, dried over sodium sulfate and evaporated to dryness. Distillation at 0.8 mm Hg gave methyl 6-bromohexanoate, b.p. 85°–90°/0.8 mm.

1-(7-Carboxyheptyl)-3-methyl-2-(2-pyridyl)indole is prepared analogous to the procedure of example 1 using as starting material the 3-methyl-2-(2-pyridyl)indole described in J. Chem. Soc. 1955, 2865.

The corresponding compounds of formula II wherein $R_1'$=hydrogen, Pyr=2-,3-, or 4-pyridyl and $R_2'$=fluoro, hydrogen or methyl are similarly prepared, using the procedures of examples 1 and 2, from the prerequisite ω-bromo ester and the following known starting 2-(pyridyl)indoles: the 2-(2-,3- and 4-pyridyl)-indoles described in Pharm. Bull. Japan 4, 16 (1956); and 5-(fluoro and methyl)-2-(3-pyridyl)indoles described in Bull. Soc. Chim. France 1969, 4154.

EXAMPLES 7 and 8

The following compounds of formula II in which $R_1'$=CH$_3$; Pyr=3-pyridyl; $C_mH_{2m}$=(CH$_2$)$_5$ and $R_4$=OH were prepared

| Example | $R_2'$ | M.P., °C. | Salt |
| --- | --- | --- | --- |
| 7 | 5-Cl | 143–5 | — |
| 8 | 5-OCH$_3$ | 175–8 | HCl |

The compound of example 7 is prepared as follows:

To a suspension of 1.39 g of a 50% sodium hydride suspension in mineral oil dissolved in 30 ml of dimethylformamide was added under nitrogen at 0°–5° dropwise while stirring a solution of 6.59 g of 5-chloro-3-methyl-2-(3-pyridyl)indole (prepared as described in U.S. Pat. No. 3,468,894) in 60 ml of dimethylformamide. After addition was complete the suspension was stirred at 0° for ½ hour. While maintaining the temperature at 0° a solution of 6.06 g of methyl 6-bromohexanoate in 10 ml of dimethylformamide was added dropwise. The reaction mixture was allowed to reach room temperature and was stirred at room temperature for 5 hours, and poured into 400 ml of ice water. The resulting mixture was extracted with ethyl acetate (3×300 ml). The ethyl acetate extract was washed with saturated sodium chloride solution, dried over magnesium sulfate and evaporated to dryness to give 1-(5-methoxycarbonylpentyl)-5-chloro-3-methyl-2-(3-pyridyl)indole as an oil.

A solution of 3.2 g of the above ester in 30 ml of 3N sodium hydroxide was heated under reflux for 17 hours. After cooling the resulting product was collected by filtration, and dissolved in 50 ml of water. Acidification with 2N HCl to pH 4–5 precipitated the product which was purified by suspending in ether to give 1-(5-carboxypentyl)-5-chloro-3-methyl-2-(3-pyridyl)indole, m.p. 143°–5°.

Similarly prepared was 1-(5-carboxypentyl)-5-methoxy-3-methyl-2-(3-pyridyl)indole, obtained as an oil. Treatment with ethanolic hydrochloric acid in ethanol and crystallization by addition of ethyl ether yielded compound of example 8, namely 1-(5-carboxypentyl)-5-methoxy-3-methyl-2-(3-pyridyl)indole hydrochloride, m.p. 175°–8°. 1-(5-carboxypentyl)-5-hydroxy-3-methyl-2-(3-pyridyl)-indole is prepared as follows:

A solution of 1.70 g of 1-(5-carboxypentyl)-5-methoxy-3-methyl-2-(3-pyridyl)indole in 85 ml of 48% hydrobromic acid is heated under reflux for 0.5 hour. Purification of the resulting product yields 1-(5-carboxypentyl)-5-hydroxy-3-methyl-2-(3-pyridyl)indole.

EXAMPLES 9 and 10

The following examples of formula III in which $C_pH_{2p}$ represents CH$_2$CH$_2$, and Pyr represents 3-pyridyl were prepared essentially according to the procedure of example 2. Condensation of ethyl 3-methyl-2-(3-pyridyl)-indole-5-propionate with ethyl 6-bromohexanoate and methyl 8-bromooctanoate respectively yielded the esters of examples 9a and 10a. Hydrolysis with hydrochloric acid gave the resulting diacids of examples 9 and 10.

| Example | CnH2n | M.P., °C. | R5 | R6 | Recrystallization Solvent |
|---------|-------|-----------|-----|-----|---------------------------|
| 9a | (CH2)5 | oil | OC2H5 | OC2H5 | — |
| 9 | (CH2)5 | 143–5 | OH | OH | acetonitrile |
| 10a | (CH2)7 | oil | OCH3 | OC2H5 | — |
| 10 | (CH2)7 | 128–30 | OH | OH | acetonitrile |

1-Carboxyheptyl-3-methyl-2-(4-pyridyl)-3-methyl-indole-5-propionic acid is similarly prepared.

The starting indoles were prepared as follows:

To a suspension of p-hydrazinohydrocinnamic acid (Manske and Kulka, J. Can. Res., 25B: 376 (1947), 4.50 g) in 50 ml of absolute ethanol under nitrogen at room temperature was added while stirring 10 ml of a saturated ethanolic hydrogen chloride solution. A solution resulted in approximately 5 minutes. To the red-orange solution was added 3-propionylpyridine (3.37 g, 0.025 mole), the reaction mixture was heated to reflux and maintained at reflux for 18 hours. The resulting solution was cooled in an ice-water bath and the resulting yellow crystals of ethyl 3-methyl-2-(3-pyridyl)indole-5-propionate hydrochloride were collected, m.p. 249°–51°. The free base, ethyl 3-methyl-2-(3-pyridyl)indole-5-propionate was prepared by suspending the hydrochloride salt in water, basifying with 3N sodium hydroxide and extracting with ether.

Similarly prepared was ethyl 3-methyl-2-(4-pyridyl)-indole-5-propionate hydrochloride, m.p. greater than 275°, and the corresponding free base.

Heating a suspension of ethyl 3-methyl-2-(3-pyridyl)indole-5-propionate hydrochloride in 450 ml of 2N HCl at reflux temperature for 2 hours, cooling and collecting the resulting solid gave 3-methyl-2-(3-pyridyl)-indole-5-propionic acid hydrochloride, m.p. 290°. Similar hydrolysis of ethyl 3-methyl-2-(4-pyridyl)indole-5-propionate yielded 3-methyl-2-(4-pyridyl)indole-5-propionic acid hydrochloride, melting above 305°.

EXAMPLE 11

A solution of 1-(4-cyanobenzyl)-3-methyl-2-(3-pyridyl)-indole (5.8 g) in 100 ml of a 1:1 mixture of 20% aqueous hydrochloric acid and glacial acetic acid was heated at reflux for 20 hours. After cooling, the solution was poured into ice water (100 ml) and the pH was adjusted to 4.5–5 with saturated sodium bicarbonate solution. The resulting precipitate was extracted with ethyl acetate, the ethyl acetate extract was washed with water and evaporated to dryness to give 1-(4-carboxybenzyl)-3-methyl-2-(3-pyridyl)indole, m.p. 273°–5°.

The starting nitrile was prepared as follows:

To a suspension of 2.9 g (0.06 mole) of 50% sodium hydride in mineral oil in 40 ml of dimethylformamide under nitrogen at 0°–5° was added dropwise over 20 minutes a solution of 10.4 g (0.05 mole) of 3-methyl-2-(3-pyridyl)indole in 60 ml of dimethylformamide. The reaction mixture was stirred for 0.5 hour at 0°–5° followed by dropwise solution of 9.8 g (0.05 mole) of p-cyanobenzyl bromide in 50 ml of dimethylformamide. After stirring at 0°–10° for 1 hour and at room temperature for 0.5 hour, the reaction mixture was poured into ice-water (600 ml). The resulting solid was collected, dried, washed with petroleum ether and redissolved in ether (500 ml). The ether solution was first washed with water, then with saturated sodium bicarbonate solution, dried over MgSO4, treated with charcoal and filtered. Evaporation of the ether extract to dryness yielded a yellow solid. This product was slurried in hot cyclohexane and collected by filtration to give 1-(4-cyanobenzyl)-3-methyl-2-(3-pyridyl)indole, m.p. 127°–9°.

EXAMPLE 12

To a suspension of 0.49 g of lithium aluminum hydride in 50 ml of anhydrous tetrahydrofuran under nitrogen was added dropwise at room temperature a solution of 3.92 g of 1-(5-methoxycarbonylpentyl)-5-chloro-3-methyl-2-(3-pyridyl)indole in 30 ml of anhydrous tetrahydrofuran. After addition was complete the suspension was stirred for 1 hour at room temperature, and 50 ml of a saturated ammonium chloride solution was added. The reaction mixture was allowed to stand at room temperature overnight and the organic layer was separated. The aqueous layer was filtered to remove salts and extracted with ethyl acetate (2×50 ml). The combined organic layers were washed with saturated brine, dried over magnesium sulfate and concentrated in vacuo. The crude product was purified by trituration with hexane/ether and dissolved in ethanol. Ethanolic hydrochloric acid was added to acidity and the solution diluted with anhydrous ether to crystallize the product. 1-(6-Hydroxyhexyl)-5-chloro-3-methyl-2-(3-pyridyl)indole hydrochloride hemihydrate, m.p. 115°–8° was obtained.

EXAMPLE 13

To a suspension of 1.52 g of 1-(5-carboxypentyl)-5-chloro-3-methyl-2-(3-pyridyl)indole in 50 ml of toluene under nitrogen was added dropwise at room temperature 0.31 ml of thionyl chloride. The resulting mixture was heated under reflux for 1 hour. An additional 0.10 ml portion of thionyl chloride was added and the solution was stirred at room temperature overnight. The resulting suspension was evaporated to dryness to give crude 1-(5-chlorocarbonylpentyl)-5-chloro-3-methyl-2-(3-pyridyl)indole which was used directly without further purification. A suspension of 0.86 g of the above 1-(5-chlorocarbonylpentyl)-5-chloro-3-methyl-2-(3-pyridyl)indole in 20 ml of concentrated ammonium hydroxide was stirred at room temperature overnight. Filtration of the suspension and slurrying of the resulting solid in ethyl ether yielded 1-(5-carbamoylpentyl)-5-chloro-3-methyl-2-(3-pyridyl)indole, m.p. 137°–40°.

EXAMPLE 14

To a suspension of 2.9 g (0.06 mole) of 50% sodium hydride in mineral oil in 40 ml of dimethylformamide under nitrogen at 0°–5° is added dropwise over 20 minutes a solution of 10.4 g of 3-methyl-2-(3-pyridyl)indole in 60 ml of dimethylformamide. The mixture is stirred for 0.5 hour at 0°–5° followed by the dropwise addition of 17.6 g (0.06 mole) of 1-tetrahydropyranyloxy-8-bromooctoane in 50 ml of dimethylformamide. After stirring at 0°–10° for 1 hour and at room temperature for 0.5 hour, the reaction mixture is poured into ice-water and extracted with ether. The ether extract is washed with water, dried over MgSO4 and evaporated to dryness. The residue is dissolved in 100 ml of 3N hydrochloric acid, the resulting mixture is kept at room temperature for 0.5 hour, washed with ether, basified with aqueous with 3N sodium hydroxide solution and extracted with methylene chloride. The methylene chloride solution is evaporated to dryness to give 1-(8-hydroxyoctyl)-2-(3-pyridyl)-3-methylindole.

EXAMPLE 15

A solution of 4 g of 1-(7-methoxycarbonylheptyl)-3-methyl-2-(3-pyridyl)indole in 40 ml of n-butanol is saturated with methylamine and heated on a steam bath in a pressure bottle for 3 days. The reaction mixture is evaporated to dryness and the product is crystallized to yield the 1-[7-(N-methylcarbamoyl)heptyl]-3-methyl-2-(3-pyridyl)indole.

EXAMPLE 16

Preparation of 10,000 tablets each containing 10 mg of the active ingredient of Example 1:

| Formula: | |
| --- | --- |
| 1-(7-carboxyheptyl)-3-methyl-2-(3-pyridyl)indole | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave with 6.4 mm diameter, uppers bisected.

EXAMPLE 17

Preparation of 10,000 capsules each containing 25 mg of the active ingredient of Example 11:

| Formula: | |
| --- | --- |
| 1-(4-carboxybenzyl)-3-methyl-2-(3-pyridyl)indole | 250.0 g |
| Lactose | 1,650 g |
| Talcum powder | 100.0 g |

Procedure:

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

What is claimed is:

1. A compound of the formula

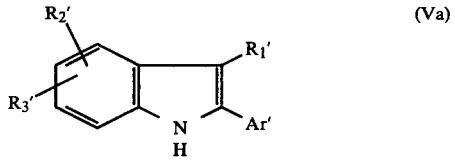

wherein
$R_1'$ represents hydrogen or lower alkyl;
$Ar'$ represents pyridyl;
$R_2'$ represents carboxy lower alkyl, lower alkoxycarbonyl lower alkyl, carboxy or lower alkoxycarbonyl; and
$R_3'$ represents hydrogen.

2. A compound of claim 1 wherein $R_2'$ is attached at the 5 position of the indole nucleus.

* * * * *